(12) United States Patent
Kochel

(10) Patent No.: US 6,312,602 B1
(45) Date of Patent: *Nov. 6, 2001

(54) PEPTIDE-CONTAINING COMPOSITIONS, AND METHODS OF MAKING AND USING SAME

(76) Inventor: Bonawentura Kochel, Ul. Tragutta, 57/59 Wroclaw (PL), 50417

( * ) Notice: Subject to any disclaimer, the term of this patent is extended or adjusted under 35 U.S.C. 154(b) by 0 days.

This patent is subject to a terminal disclaimer.

(21) Appl. No.: 09/212,174

(22) Filed: Dec. 15, 1998

Related U.S. Application Data

(63) Continuation-in-part of application No. 08/726,650, filed on Oct. 7, 1996, now Pat. No. 5,849,196.

(51) Int. Cl.[7] .......................... B01D 61/24; A61K 35/14; A61K 35/20; A61K 35/72
(52) U.S. Cl. .......................... 210/651; 424/520; 424/529; 424/535; 514/2; 514/7; 514/44
(58) Field of Search .......................... 210/651; 424/520, 424/529, 535; 435/91.1; 514/2, 7, 21, 44, 885

(56) References Cited

U.S. PATENT DOCUMENTS

| | | | | |
|---|---|---|---|---|
| 5,807,839 | * | 9/1998 | Hirschman | 514/44 |
| 5,807,840 | * | 9/1998 | Hirschman | 514/44 |
| 5,849,196 | * | 12/1998 | Kochel | 210/651 |
| 5,902,786 | * | 5/1999 | Bregmann | 514/2 |

* cited by examiner

*Primary Examiner*—John L. LeGuyader
*Assistant Examiner*—Thomas G. Larson
(74) *Attorney, Agent, or Firm*—Carrier, Blackman & Associates, P.C.; Joseph P. Carrier; William D. Blackman

(57) ABSTRACT

A first preferred peptide containing composition has therapeutically beneficial components, i.e., which heighten the phagocytic activity of neutrophils, consisting of molecules with a molecular weight of at least 8 kDa, and preferably at least 15 kDa. The beneficial components comprise peptides which will absorb light at an absorption band of $\Delta\lambda=200-235$ nm, $\lambda_{max}=205$ nm, in the UV spectrum. The preparation is nontoxic and is formulated using casein, blood albumin, beef peptone, nucleic acid (RNA) and a base such as sodium hydroxide. The preparation stimulates phagocytic activity of neutrophils, if used at sufficient concentrations. A second preferred preparation is obtained using the same components of manufacture, but filtering or centrifuging the preparation to provide a composition containing components exclusively having a molecular weight of <8–15 kDa which inhibits phagocytic activity of neutrophils.

10 Claims, 3 Drawing Sheets

PEPTIDE-CONTAINING COMPOSITIONS, AND METHODS OF MAKING AND USING SAME

CROSS-REFERENCE TO RELATED APPLICATIONS

The present application is a continuation-in-part of U.S. patent application Ser. No. 08/726,650, filed Oct. 7, 1996, now issued as U.S. Pat. No. 5,849,196.

BACKGROUND OF THE INVENTION

1. Field of the Invention

The invention relates to novel compositions containing peptides, which are useful as antiviral agents, and as agents useful in treating auto immune diseases, and to methods of making and using same. More particularly, the invention pertains to modified formulations, of the type described, with an improved ability to stimulate phagocytosis in humans for treatment of viruses and the like, and to methods of making and using same.

2. Description of Background Art

In the art there is at least one conventionally known formulation containing peptides and peptones, which is distributed under the trademark Reticulose™, which has been used as antiviral agent for humans in relation to treatment of viral infections/diseases such as influenza, herpes, infectious mononucleosis, hepatitis A and B, and most recently HIV. The known formulation is referred to as "conventional peptide-peptone composition" hereinafter.

U.S. Pat. No. 5,420,472 has recently issued on what is believed to be a method of using the conventional peptide-peptone composition to treat a specific disease. The disclosure of U.S. Pat. No. 5,420,472 is hereby incorporated by reference.

See also Anderson R. H. & Thompson R. N., Treatment of Viral Syndromes With A Lipoprotein Nucleic Acid Formulation (Reticulose), VIRGINIA MED. MONTH. 84, 347–353, 1957; Wegryn S. P., Marks R. A. and Baugh J. R., Herpes Gestations, Am J. Obst. & Gynecol. 79, 812–814, 1960; Reynolds M. R., Generalized Vaccinia Successfully Treated With Lipoprotein-Nucleic acid Complex (Reticulose) Arch Pediatrics 77, 421–422,1960; Medoff L. R. Use Of A Lipoprotein-Nucleic Acid Formulation In Treatment Of Infectious Mononucleosis, Clin. Med. 69, 1–4, 1962; Catterall R. A., A New Treatment Of herpes Zoster, Vaccinia And Chicken Pox, J. Roy. Coll. Gen. Practit. 19, 182–183, 1970; Friedland B., In Vitro Antiviral Activity Of A Peptide-Nucleic Acid Solution Against The Human Immonodeficiency Virus And Influenza A Virus, J. Royal Soc. Health 111, 170–171, 1991; Hirschman S. Z. and Chen W., Peptide Nucleic Acids Stimulate Gamma Interferon And Inhibit Replication Of Human Immunodeficiency Virus, Proc. Biomedicine '96, Washington D.C., U.S.A., May 3–6, 1996. Thompson R. M., A Lipo-Protein Nucleic Acid Complex In The Treatment Of radiation Injury, The Military Surgeon, 110, 51–58, 1952; Strickland W. N., Summary Of peptide-Nucleic acid Studies Conducted at The University of Wisconsin Biotechnology Center, Reticulose, Commonwealth Pharmaceuticals, Trenton, 1995, pp. 19–35; Friedland, B., In Vitro Antiviral Activity of a Pepti-Nucleic Acid Solution Against The Human Immunodeficiency Virus and Influenza Virus, J. ROY SOC. HEALTH, V. 111, No. 5, PP170, 171, 1991; and Cohen M. The Efficacy of a Pepti-Nucleic Acid Solution (Reticulose™) For The Treatment of Hepatitis A and Hepatitis B-A Preliminary Controlled Human Clinical Trial, J. ROY SOC. HEALTH, V. 112, No. 6, PP. 266–270 1992.

The conventional composition containing peptides and peptones, also generally referred to as nucleophosphoprotein and a lipoprotein nucleic acid solution, was originally conceived by Dr. Vincent LaPenta around 1934 and was commercially available in the U.S. for a lengthy period, ending in 1962. The conventional composition containing peptides and peptones is known to be formulated through a mixture of casein, beef peptone, ribonucleic acid (RNA), beef serum (blood) albumin, sodium hydroxide and distilled water which is processed through heat, pressurization and filtration to a solution that is of such a small molecular weight as to be compatible with any human blood type, as discussed further hereinbelow. Essentially, the conventional composition is a peptide-peptone solution in which peptone fragments are combined with short chain peptides, and wherein the molecular weight of the active components ranges from approximately 1 to 25 kDa. Presently, the conventional composition is still manufactured according to its original formulation by Advanced Viral Research Corp., in Miami, Fla. This composition was formerly believed and understood to contain peptides and nucleic acids, and thus was previously referred to as being in the class of peptide-nucleic acids (PNAs), but the thinking on this has been reevaluated, and it is no longer clear that the final product contains nucleic acids.

Although the exact nature of the antiviral activity caused by compositions such as the conventional composition containing peptides and peptones is unknown, it appears to act either by an ability to inhibit the viruses or by alteration of a host cell response in preventing virus multiplication, and a capacity to increase antiviral, antibody response in humans, which exerts a positive therapeutic effect in both acute and chronic infection. Also very significantly, the conventional peptide-peptone composition has been shown to be substantially free from side effects and systemic toxicity, unlike most other antiviral agents, including AZT and beta interferon.

Although the conventional peptide-peptone has certain advantageous characteristics as discussed above, its effectiveness as antiviral agent is known to be limited and erratic, especially when compared to other known antiviral agents including AZT, Ribavarin, Dideoxyadenosine (DDI) and Dideoxycytidine (DDC). There remains a need in the art for an antiviral agent which is, like the conventional peptide-peptone composition, substantially free of ill side effects and systemic toxicity, but which also has improved effectiveness as an antiviral agent in comparison to the conventional peptide-peptone composition.

SUMMARY OF THE INVENTION

The present invention has been developed to fulfill the above-discussed need in the art.

According to a first preferred embodiment of the invention, there is provided a peptide peptone formulation whose active components consist essentially of molecules having a molecular weight in a range from at least about 8 kDa to about 25 kDa. Preferably, the formulation comprises peptides without aromatic portions, and has an absorption band in the interval of $\Delta\lambda=200-235$ nm, with a maximum absorbtion at $\lambda_{max}=205$ nm. Most preferably, the formulation according to the invention will stimulate phagocytic activity of neutrophils above a predetermined quantity of the formulation.

Applicant has determined that the conventional peptide-peptone composition, which contains active components with a molecular weight ranging from approximately 1 to 25 kDa, exhibits a phenomenon of inhibition of neutrophil phagocytic activity in humans by different groups of active components contained therein.

Surprisingly, when the conventional peptide-peptone composition is separated into two fractions, according to the molecular weight of the components thereof, applicant has discovered that the primary antiviral activity of the peptide-peptone composition is caused by heavier molecules (MW>8–15 kDa), in the portion of the composition which will be called Fraction A throughout the present specification, including peptides without aromatic components, which stimulate phagocytosis.

Conversely, a peptide-peptone-concentration dependent inhibition is caused by small peptone fragments, which appear to be associated with peptides containing aromatic amino acids (MW<8–15 kDa), working as phagocytosis inhibitors. This lighter weight fraction of the composition will be referred to throughout the present specification as Fraction B.

Based on such discovery, applicant has modified the conventional peptide-peptone composition by separating the composition into two new compositions based on the molecular weight of the components thereof, a first composition (Fraction A) containing those active components with the molecular weight greater than 8–15 kDa so that the resulting or modified peptide-peptone formulation exhibits mainly stimulatory effects on the phagocytic activity of neutrophils, and a second composition (Fraction B) containing those active components with a molecular weight of 8 kDa or less.

Specifically, applicant has discovered that the refined peptide-peptone formulations of Fraction A according to the invention function as priming factors which convert neutrophils to a status more "respondent" to external stimuli such as N-formyl-L-methionyl-L-leucyl-L-phenylalanine (FMLP).

Further, although the lower weight active components (MW<8–15 kDa) of the modified peptide-peptone formulation of Fraction B are not effective as antiviral agents, they are effective in treating auto immune diseases such as non-Hodgkins Lymphoma, adult onset Leukemia, AIDS, Lupus, Scleraderma, Epstein Barr Virus, Cytomegalovirus, Chronic Fatigue Syndrome, Candidiasis, Rheumatoid and Osteo Arthritis, etc.

Thus, the active components of the conventional Peptide-peptone composition may be segregated according to molecular weight, and the different resulting groups of components may be selectively used to treat different viruses and auto immune diseases accordingly.

According to another important aspect of the invention there is also provided a method of preparing a Peptide-peptone formulation, comprising the steps of:

combining casein, blood albumin, beef peptone, nucleic acid and a base such as sodium hydroxide in a solution of distilled water; processing the solution under elevated temperature and elevated pressure to associate peptone and peptide components of the solution; and filtering or centrifuging the processed solution to separate out active components having a molecular weight of less than 8 kDa. Preferably, the filtering step will be performed in multiple stages, including an initial filtering or centrifuging stage comparable to that used in making the conventional Peptide-peptone formulation, which results in a solution having active components of varying molecular weights ranging from approximately 1 to 25 kDa, and a secondary filtering or centrifuging stage in which the thus filtered solution is further filtered through a semipermeable membrane such that the resulting formulation includes a first fraction which contains active components having molecular weight exclusively in a higher range of approximately 15–25 kDa, and a second fraction contains smaller molecular weight components which include aromatic compounds.

Again, it is preferred that the active components of the peptide-peptone formulation according to the first embodiment of the invention, thus processed, will include peptides having no aromatic components, and the active ingredients will absorb light in a band of $\Delta\lambda=200-235$ nm, $\lambda_{max}=205$ nm, A=0.06 in the UV spectrum.

Still further, according to another aspect of the invention there is provided a method of using a peptide-peptone formulation whose active components consist essentially of molecules having a molecular weight of at least 8, and most preferably 15, kDa as an antiviral agent, comprising the steps of:

Have blood tests performed for Hepatitis B or suspected pathogen- include IGG, IGA where approptiate.

a) Inject an effective amount of peptide-containing solution (Immax A)—subcutaneously two times daily for 7 days.

b) Inject half of original amount of peptide-containing solution—once daily for the duration of treatment.

An effective amount of the peptide-containing solution administered in step (a) may be, e.g., 1 ml per dose, depending on the virus being treated.

Do respective blood work 2 months after protocol has been completed to reevaluate condition, and adjust per attending physician's recommendation.

Usage of 1 ml 28 or 29 gauge disposable insulin-type syringes is recommended, and each syringe should be disposed of safely after a single use. The Peptide-peptone solution must be kept out of direct sunlight and may initially be refrigerated, though it need not be. If so, bring the syringe to body temperature before injection (e.g. holding it in hand). Inject slowly to provide painless infusion. If there is pain at injection site because of cold Peptide-peptone or too fast injection, pain will dissipate within 15 minutes. Rotate injection sites. Dosage schedule should be suggested, initiated and monitored by a licensed physician in all cases.

The treatment method or protocol according to the invention is effective in treating many viruses, and is often effective in completely eradicating the virus in the patient. Where the virus has not been completely eradicated, additional treatment of the virus with the formulation can be determined and tailored to the patient to the testing in step (f). The Fraction A peptide formulation according to the invention has mainly stimulatory effects on the phagocytic activity of neutrophils in the human body, and with the initial larger doses provided in steps (a) and (c), the patient often promptly realizes significant relief from the viral infection.

It is an object of the present invention to provide a peptide-peptone formulation which provides a mainly stimulatory effect, and another peptide-peptone formulation which provides a mainly inhibitory effect on phagocystic activity of neutrophils in humans, and which otherwise has substantially no toxicity or ill side effects associated therewith.

It is another object of the invention to provide a relatively simple method of preparing stable solutions of the formulation.

It is a further object of the invention to provide a protocol for treating various viruses in humans using the formulation.

It is yet another object of the invention to provide an improved peptide-peptone formulation which is tailored or modified to treat different viruses, auto immune diseases and the like.

Other objects, advantages and salient features of the invention will be apparent from the following detailed description which, in conjunction with the annexed drawings, discloses presently preferred embodiments of the invention.

DETAILED DESCRIPTION OF THE PREFERRED EMBODIMENTS

Preparation of Conventional Peptide-Peptone Formulation

Figure 1:
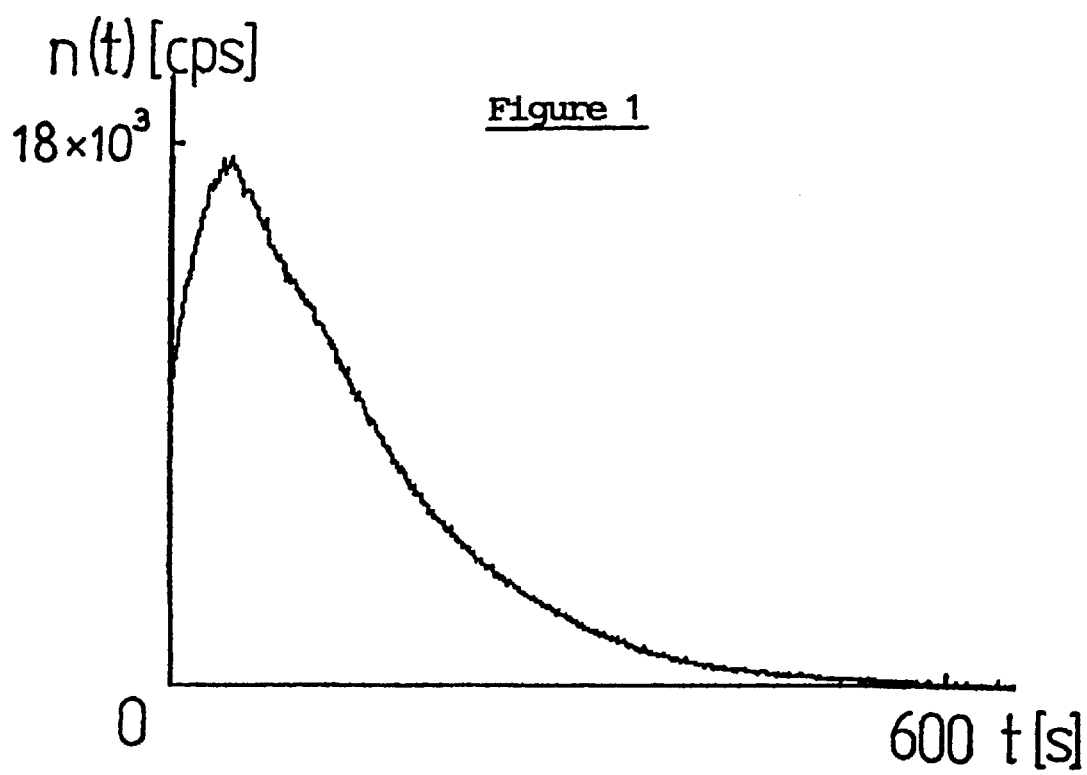
FIG. 1 is a photon-counting time series representing the time-resolved phagocyte luminescence of isolated native human neutrophils stimulated with FMLP.

According to a known process, the known peptide-peptone formulation has been prepared over a period of days in the following manner.

First, the indicated quantities of the following components are mixed into ten liters of distilled water under slow stirring:

| RAW MATERIALS | AMOUNTS | WEIGHT PERCENTAGE |
| --- | --- | --- |
| casein | 250 grams | 43.9% |
| blood albumin | 15 grams | 2.6% |
| beef peptone | 150 grams | 26.3% |
| nucleic acid (RNA) | 80 grams | 14.0% |
| sodium hydroxide | 75 grams | 13.2% |

After the ingredients are sufficiently dispersed in the distilled water, the solution is processed under elevated temperatures and pressure using a steam autoclave at a pressure of approximately 5–15 p.s.i. over a period of approximately 2–10 hours. After the heat and pressure treatment, the solution is then cooled to a temperature somewhat below room temperature and allowed to set until the following day.

The following day the solution is then filtered under an argon gas atmosphere, first through an Ertel asbestos pad filter (#0.40 or equivalent) after which the pH of the solution is adjusted to approximately 8.5 and the solution is again filtered through a #nine (9) filter pad, after which the solution is then adjusted to pH of approximately 7.8 and again filtered through an Ertel #. EO pyrogen retention filter pad. Again, the filtered solution is refrigerated and stored until the following day. Argon gas is preferred for the gas atmosphere because it is somewhat easier to handle than other gases such as nitrogen, and because its inert nature assures sterility of the resulting formulation.

On the third day, the solution is diluted to an appropriate nitrogen content and its pH adjusted to approximately 7.5, after which the solution is passed through a millipore filter HA (0.45 $\mu$) for final filtration, after which it is ready for packaging and use.

The Peptide-peptone formulation thus formed is typically stored in sealed glass ampules under an argon gas atmosphere, in appropriate quantities such as 2, 5 ml and 10 ml vials.

Preparation Of The Modified Peptide-Peptone Formulation Of The Invention

The peptide-peptone formulation according to the invention is similar to the conventional peptide-peptone formulation except that it is additionally or more specifically filtered or centrifuged to remove or separate lower molecular weight active components from higher molecular weight components. The formulation according to the invention may be obtained by further processing the conventional peptide-peptone formulation.

According to the present invention, the conventional peptide-peptone formulation is preferably further processed by a dialysis thereof through a semi-permeable membrane having an average pore radius of approximately 10–40 Angstroms, and most preferably having an average pore radius of 24 Angstroms. Alternatively, the further processing of the conventional peptide-peptone formulation could be effected using appropriate centrifugation techniques. Appropriate semipermeable membranes or dialysis tubing may be acquired from Viskin of Serva Germany. The threshold for molecular weight (MW) of molecules removed or separated by dialysis according to the invention is in the range of 8–15 kDa, and most preferably all molecules with an MW of <15 kDa. Applicant has discovered that the heavier active components remaining in the modified or dialyzed Fraction A peptide formulation according to the invention, MW>15–25 kDa and including peptides without aromatic components, stimulate phagocytosis of the neutrophils in humans when applied above a certain quantity thereof; and that the smaller active components of Fraction B, removed from the peptide-peptone formulation through dialysis, including small peptone fragments associated with peptides containing aromatic amino acids and having molecular weights in the range of approximately 1–15 kDa, normally function as phagocytosis inhibitors at all concentrations thereof.

Additionally, applicant has discovered that the conventional peptide-peptone formulation exhibits a phenomenon of modulation of the neutrophil phagocytic activity caused by the interplay between the lower molecular weight components (<8–15 kDa) and the larger components (>8–15 kDa, i.e., the smaller components inhibit the stimulatory effect of the larger components.

Correspondingly, in the modified Fraction A peptide formulation according to the invention, the smaller active components are removed, so that the full stimulatory effect of the larger active components is achieved, while the inhibitory effect of the smaller active components is avoided.

Moreover, it is believed that the smaller active components of Fraction B may be used in treating auto immune diseases.

Moreover, even within the range of larger, stimulating active components present in Fraction A, applicant has been able to isolate narrower ranges of the active components which are more effective in treating different viruses, such as HIV, influenza, herpes, etc.

The much enhanced effectiveness of the Fraction A peptide formulation according to the invention as an antiviral agent is demonstrated by the following in vitro tests conducted by applicant comparing the Fraction A peptide formulation according to the invention with the conventional Peptide-peptone formulation. Measurements in the testing procedure were made using a single photon-counting method in order to record the time-resolved phagocyte luminescence or chemiluminescence of human isolated neutrophils. Such luminescence was first observed in 1972 and has been used since as an effective measurement of phagocytic activity and the like. Allen R. C.

Stjernholm R. L., and Stele R. H., Evidence Of The Generation of(An) Electronic Excitation State(s) in Human Polymorphonuclear Lukocytes And Its Participation in Bacterial Activity, *Biochem. Biophys. Res. Commun.*, 47, 679–684, 1972. The phagocyte luminescence, a phenomenon, involves reaction of certain products of oxygen reduction generated by stimulated neutrophils or other cells. As discussed above, it is believed that the conventional Peptide-peptone formulation and the modified Fraction A formulation according to the invention enhances the leukocytic response, increases antibody production and stimulates phagocytosis of human neutrophils, and the inventors sought to verify this thesis of phagocytic function of neutrophil by means of a single photon-counting technique applied to a time-resolved phagocytic luminescence of isolated human neutrophils incubated with the Peptide-peptone formulations and then stimulated with FMLP.

Applicant's testing, as described fully below, not only verifies the thesis, but shows that the Fraction A peptide formulation according to the invention functions as a potent stimulator of phagocytosis in human neutrophils.

EXAMPLE 1

EFFECTS OF PEPTIDE-PEPTONE COMPOSITIONS ON NEUTROPHIL PHAGOCYTOSIS, AS MEASURED BY CHEMILUMINESCENCE MEASUREMENTS

Material and Method

Experimental material consisted of human neutrophils obtained from venous blood of fifteen adult healthy subjects, then isolated according to Böyum's method. See Böyum A; Isolation of Lymphocites, Granulocytes and Macrophages, Scand. *J. Immnunol.* 5 (Supp 5), 9–15, 1976. The cells were counted in a Bürker's chamber and their types were determined by a Pappenheim staining procedure. The cell samples contain over 90 percent mature neutrophils, their viability evaluated by a trypan blue (1% solution in 0.15 M NaCl) exceeded 95 percent.

A standard buffer solution (SBS), commonly used in chemiluminescent research was composed of phosphate buffered saline (pH 7.4), 10 mM glucose and 10 mM N-[2-hydroxyethyl] piperazine-N'-[2-ethanesulfonic acid] available from Calbiochem in Switzerland.

The cell samples contain $3 \times 10^5$ neutrophils in 3 ml of SBS, were incubated at 37° C. for a period of 5 minutes with 5 microliters of the conventional Peptide-peptone formulation or of the Fraction A peptide formulation according to the invention in different concentrations. After the 5 minute incubation, luminol (a 2.5 $\mu$M final concentration), available from Koch-Light Lab in England, was added to the samples. After the next 5 minutes phagocytic processes were initiated by FMLP, available from Sigma Chemical in the United States, then chemiluminescent processes were registered at a temperature of 37° C. by means of a single photon counting technique using a M12 FQ51 photoamplifier, manufactured by Ziess of Germany.

Solutions of the Fraction A peptide formulation according to the invention as used in the testing were made by dialyzing the conventional Peptide-peptone formulation as discussed above, and particularly by dialyzing a 4 ml quantity of the conventional formulation to one liter of physiological solution during 48 hours at 4° C., and the resulting solution again consisted essentially of active components for Peptide-peptones having a molecular weight in the range of 15–25 kDa.

Given the diluted nature of the dialyzed Fraction A solution, and in order to redress the absorbance of A=0.77 in the 200–235 nm band which had been caused by a given volume (V) of the conventional Peptide-peptone formulation, it was necessary to use the dialyzed Fraction A solution of the invention at a volume 12 times as large as the volume (V) of conventional Peptide-peptone used. The larger volume of dialyzed Fraction A formulation was used in compiling data for FIG. 5.

The chemiluminscent processes have been recorded in form of photon-counting time series [n(t):t=1,2, . . . ,N], composed of the numbers of photoelectrons n(t) registered in consecutive time intervals $(t, t+\Delta t_c)$, with a counting time $\Delta t_c = 1$ s, separated by the same length intervals (constituting the dead time interval of recorder, $\Delta t_d = \Delta t_c$ during which no photoelectrons were registered). The quantity n(t) is proportional to the number of photons emitted by the light producing-system and submitted to the same statistics. An example of photon-counting time series (PCTS) describing the emission from native neutrophils stimulated by FMPL is shown in FIG. 1. Analogous PCTS, in respect to shape but not of the magnitude, occur for neutrophils incubated with the conventional Peptide-peptone formulation or with the Peptide-peptone formulation according to the invention.

RESULTS AND DISCUSSION

Effects of Conventional Peptide-peptone on Phagocytosis

An integrated intensity of emission $I = \Sigma_t n(t)$ was measured in a time interval [1,N], corresponding to a whole process (composed of ascending and descending stages). Surprisingly, the measurements show that the samples of neutrophils treated with the conventional Peptide-peptone formulation had integrated intensities ($I_p$) lower than those ($I_n$) of native or untreated neutrophils samples. In other words, a perturbation of phagocytosis, reflected by the inequality $I_p<I_n$ and corresponding to an inhibition of phagocytic activity of neutrophils, was demonstrated by the samples treated with the conventional Peptide-peptone formulation.

The effect of the conventional Peptide-peptone formulation on a phagocytic activity of neutropils was determined using the ratio $I_p/I_n$ (again refer to the Allen article discussed above) and a perturbation coefficient CPC=$(I-I_p/I_n)\cdot 100[\%]$, where the perturbation coefficient is normalized to 100% and directly proportional to the magnitude of perturbation or inhibition. See Kochel B., Time-Resolve Luminescence of Perturbed Biosystems: Scholastic Models and Perturbation Measures, *Experimentia*, 48,1059–1069, 1992. The experimental results of the samples treated with a conventional Reticulose™ formulation are shown in Table 1.

TABLE 1

| Reticulose volume per the sample*) V [μl] | Ratio of the integrated intensities $I_p/I_n$ | Perturbation measure CPC ± SD(CPC)**) [%] |
|---|---|---|
| 0.063 | 0.388 | 61.2 ± 4.9 |
| 0.063 | 0.560 | 44.0 ± 4.2 |
| 0.078 | 0.567 | 43.3 ± 4.0 |
| 0.083 | 0.466 | 53.4 ± 3.7 |
| 0.100 | 0.480 | 52.0 ± 4.5 |
| 0.125 | 0.386 | 61.4 ± 4.8 |
| 0.156 | 0.695 | 30.5 ± 3.8 |
| 0.167 | 0.734 | 26.6 ± 4.2 |
| 0.167 | 0.664 | 33.6 ± 3.3 |
| 0.200 | 0.426 | 57.4 ± 4.0 |
| 0.250 | 0.422 | 57.8 ± 4.6 |
| 0.250 | 0.401 | 59.9 ± 4.7 |
| 0.313 | 0.337 | 66.3 ± 4.1 |
| 0.500 | 0.402 | 59.8 ± 3.6 |
| 0.500 | 0.329 | 67.1 ± 3.6 |
| 0.625 | 0.188 | 81.2 ± 3.9 |
| 1.000 | 0.248 | 75.2 ± 4.1 |
| 1.000 | 0.223 | 77.7 ± 3.4 |
| 1.250 | 0.253 | 74.7 ± 4.3 |
| 1.250 | 0.228 | 77.2 ± 3.7 |
| 1.250 | 0.224 | 77.6 ± 4.5 |
| 2.500 | 0.113 | 88.7 ± 3.8 |
| 5.000 | 0.128 | 87.2 ± 4.4 |

*)Sample volume: 3 ml.
**)SD(CPC) = $10^4 \cdot N/I_n \cdot [1 + (I_p/I_n)^2]^{1/2}$ at SD(n(t)) = 100 cps.

Figure 2:
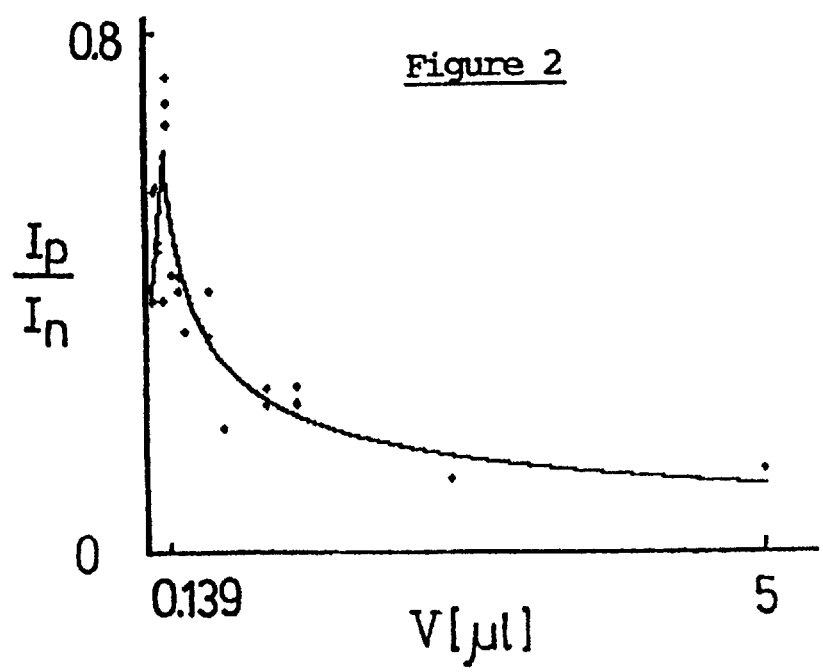
FIG. 2 is a graph depicting a nonmonotonic dependence of the $I_p/I_n$ ratio, employed as a phagocytosis perturbation measure, on the volume (V) of a conventional peptide-peptone solution, where $I_n$ refers to native (i.e., unperturbed) neutrophils, $I_p$ refers to perturbed neutrophils, and I describes the so-called integrated luminescence.

The volume V of the conventional Peptide-peptone formulation has been used as a control variable for the experiment, and a corresponding concentration of the formulation in each sample (3 ml) is expressed by the formula [volume percentage]=V[μl]/30. In the interval [0.063, 0.139] μl a linear regression of the ratio $I_p/I_n$ on V, $$I_p/I_n=(2.04\pm0.82)\cdot V+0.32\pm0.10) \quad (1)$$

is the best one (r=0.69±0.18) amongst other elementary regressions such as power (r=0.59±0.22), logarithmic (r=0.63±0.20) or exponential (r=0.64±0.20). Refer to FIG. 2 linear regression.

From Eq. 1 and the definition of CPC above, the following dependence of CPC on V results:

$$CPC=\{1-[(2.04\pm0.82)\cdot V+(0.32\pm0.10)]\}\cdot 100 \quad (2)$$

The coefficients in all the regression equations are expressed together with their standard deviations (SD).

At the volumes V>0.1391 μl a power regression of $I_p/I_n$ on V (Table I, FIG. 2), $$I_p/I_n(V)=(0.23\pm0.02)\cdot V^{-(0.49\pm0.05)} \quad (3)$$

fits better (r=0.93±0.04) the experimental data points than logarithmic (r=0.87±0.06) or exponential (r=0.76±0.11) ones. Therefore a CPC (V) function takes the form:

$$CPC(V)=[1-(0.23\pm0.02)\cdot V^{-(0.49\pm0.05)}]\cdot 100 \quad (4)$$

Figure 3:
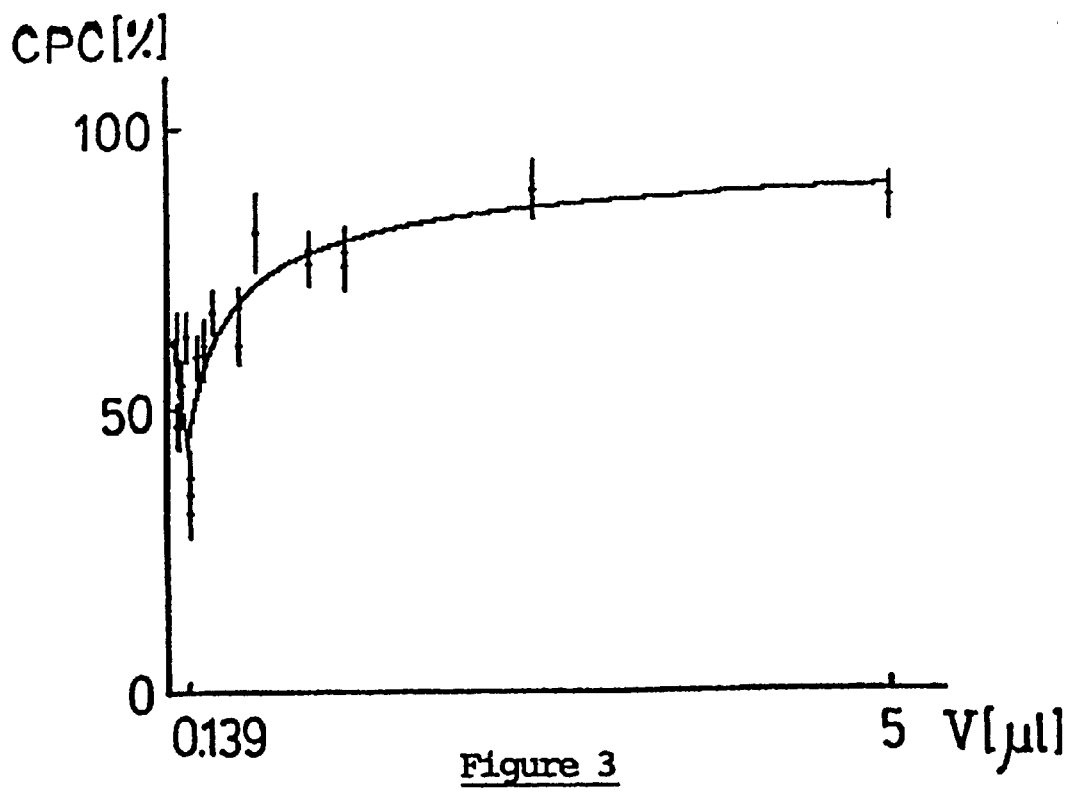
FIG. 3 is a graph showing nonmonotonic changes in the classical perturbation coefficient (CPC) describing the inhibitory effect of the conventional peptide-peptone formulations on the phagocyctic activity of isolated human neutrophils.

From Eqs. 2 and 4 it can be seen that an inhibitory effect of conventional Peptide-peptone formulation on a phagocytic activity of neutrophils decreases when the conventional Peptide-peptone volume V tends from 0.063–0.139 μl, then the inhibitory effect increases with V at V>0.139 μl as shown in FIG. 3.

The results obtained using the conventional Peptide-peptone formulation indicate an inhibition of phagocytosis in the entire volume range tested. Nonmontonic changes, similar to those induced by the conventional Peptide-peptone formulation in the inhibition of phagocytosis, observed in the CPC=CPC(V) function (FIG. 3), are also known, although unexplained, in chemiluminescence of neutrophils in the presence of plasma. Faden H., Luminol-Dependent Whole Blood Chemiluminescence Assay, *Cellular Chemiluminescence*, V. 11 K. Van Dyke and V. Castranova (Eds.), CRC Press Boca Raton 1987, pp 183–191.

Figure 4:
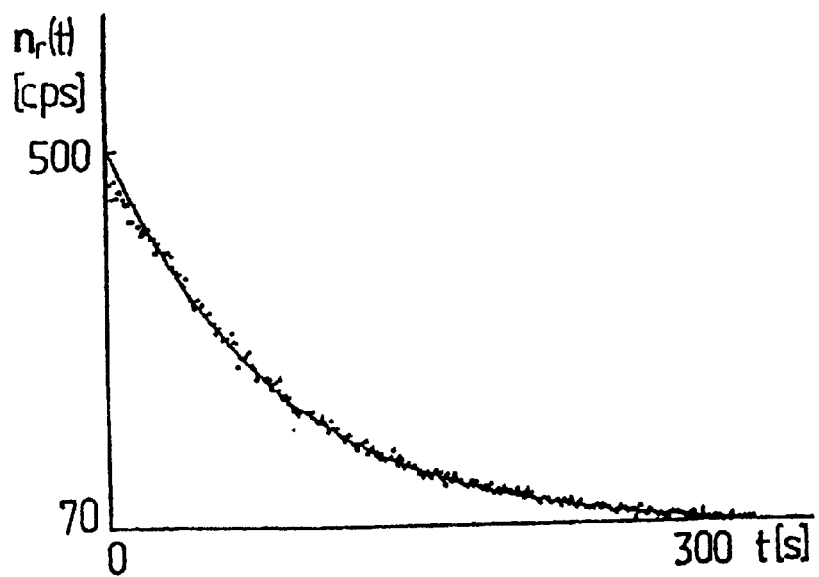
FIG. 4 is a different photon-counting times series $\{n_r(t)\}$ showing the effects on neutrophil phagocytosis induced by a given volume of the conventional peptide-peptone formulation, in which the descending stage of the $\{n_r(t)\}$ process is described as an exponential decay; $n_r(t) = (5512 \pm 64) \cdot \exp[-(1336 \pm 7) \times 10^{-5} \cdot t]$.

Additionally, it should be noted that the inhibitory effect of the conventional Peptide-peptone formulation and the neutrophil phagocytosis does not depend on the order of addition of the conventional Peptide-peptone formulation and FMLP (activator). This means that the inhibition is neither caused by the receptor-ligand interaction nor by the signal transduction to the cell. This fact and a good fitting (r=0.997±0.001) shown in FIG. 4 of the $[n_r(t)]$ series by an exponential regression, $$n_r(t)=(5512\pm64)\cdot \exp[-(1336\pm7)\times 10^{-5}\cdot t], \quad (5)$$

where $\{n_r(t)\}$ is a difference series resulting from the $\{n_n(t)\}$ series (the phagocyte luminescence of native neutrophils) by subtracting the $\{n_p(t)\}$ series (the phagocyte luminescence of neutrophils perturbed with 0.25 μl of the conventional Peptide-peptone formulation) appear to support a possibility of scavenging of oxygen radicals by peptide-peptone compositions. At k=1336 and $\Delta t_c=\Delta t_d=1$ s the solution in Eq. 5 corresponds to a first-order ($\alpha=1$) reaction with the rate constant $k_r=k\cdot \Delta t_c^{\alpha-1}\cdot 2^{-\alpha}=668$ photocount/s.

By comparing the results obtained for these samples using the conventional Peptide-peptone formulation with those discussed below obtained using the improved Fraction A peptide formulation according to the present invention, one can conclude that the inhibition obtained using the conventional Peptide-peptone formulation is caused by low-molecular weight formulations (MW<8–15 kDa) absorbing at 235–300 nm in the UV spectrum. These formulations have already been identified as nucleic acid fragments and/or nucleic acids associated with peptides. W. N. Strickland, Summary of Peptide Nucleic Acid Studies conducted at the University of Wisconsin Biotechnology Center, *Reticulose, Commonwealth Pharmaceuticals*, Trenton, 1995, pp. 19–35. One possible explanation of the inhibition can be based on the influence of these "small" molecules on the final stage of phagocytosis, i.e., they can play a role of scavengers of oxygen radicals. Such a phenomenon is known for, e.g., plasma where endogenous inhibitors of oxygen radicals quench luminescence. See the section by H. Faden in Cellular Chemiluminscent discussed above. Another alternative, and not necessarily disjunctive, explanation can be related to the influence of the conventional Peptide-peptone formulation on the early stages of phagocytosis, e.g., the receptor expression, certain metabolic pathways, etc.

Effects Of The Improved Fraction A Peptide Formulation On Phagocytosis

Figure 5:
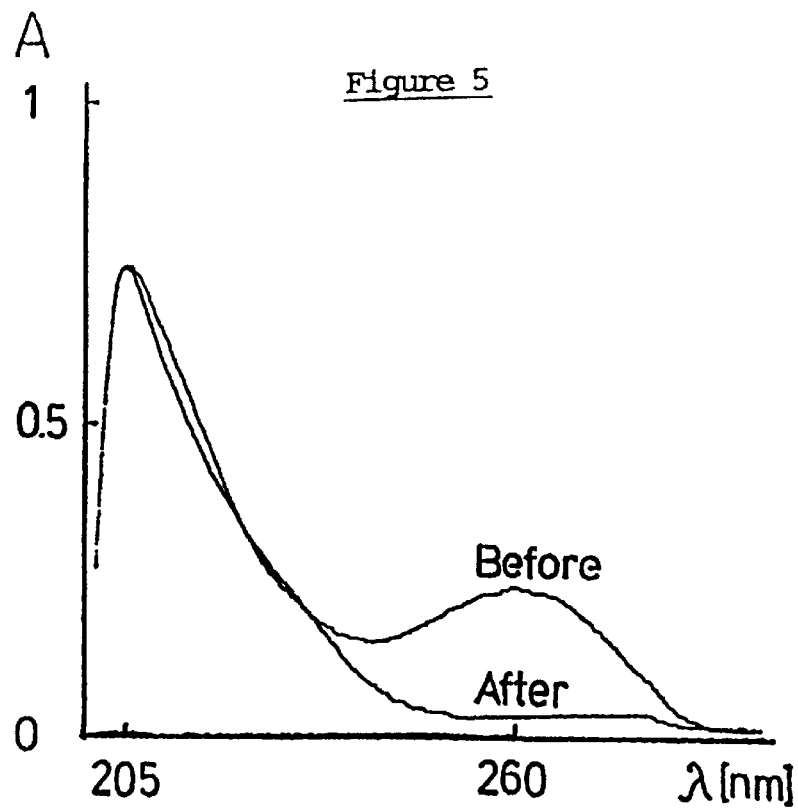
FIG. 5 is an absorption spectrum in the UV range of a conventional peptide-peptone formulation and a corresponding absorption spectrum in the UV range of a peptide-peptone formulation according to the present invention.

As discussed above, the improved Fraction A peptide formulation according to the invention contains active components/molecules with molecular weight greater than 8–15 kDa, preferably in a range of 15–25 kDa, and which are characterized by an absorption band ($\Delta\lambda$=200–235 nm, $\lambda^{max}$=205 nm, A=0.06) in the UV spectrum as shown in FIG. 5. By comparison, a sample of the conventional Peptide-peptone formulation at the same absorption band (200–235 nm) has an absorption of A=0.77. In order to redress such absorbance of the conventional Peptide-peptone formulation in the samples involving the improved Fraction A peptide formulation according to the invention, it is necessary to use the improved Fraction A peptide formulation in a volume of $V_D$=12•V, where V is a given volume of the conventional Peptide-peptone formulation. Results of the tests involving the improved Fraction A peptide formulation according to the invention are set forth in Table 2 below.

TABLE 2

| Equivalent Reticulose volume*) per the sample**) V [µl] | Ratio of the integrated intensities $I_p/I_n$ | Perturbation measure CPC ± SD(CPC) [%] | Remarks |
| --- | --- | --- | --- |
| 0.167 | 0.648 | 35.2 ± 5.3 | Inhibition of phagocytic activity of neutrophils |
| 0.420 | 0.476 | 52.4 ± 4.4 | |
| 0.830 | 0.452 | 54.8 ± 2.4 | |
| 0.830 | 0.436 | 56.4 ± 3.7 | |
| 1.250 | 0.292 | 70.8 ± 9.7 | |
| 2.500 | 0.751 | 24.9 ± 3.7 | |
| 2.500 | 0.925 | 7.5 ± 4.5 | |
| 2.500 | 1.051 | −5.1 ± 4.7 | Stimulation of phagocytic activity of neutrophils |
| 5.000 | 1.220 | −22.0 ± 4.6 | |
| 5.000 | 1.359 | −35.9 ± 4.8 | |
| 10.000 | 1.512 | −51.2 ± 8.3 | |
| 10.000 | 1.974 | −97.4 ± 4.4 | |
| 20.000 | 3.454 | −254.4 ± 9.2 | |

*)A given volume ($V_D$) of the Reticulose dialysate has been expressed by the equivalent volume of Reticulose (V) causing the same absorbance at 205 nm.
**)Sample volume; 3 ml.

Generally speaking, CPC>0 at $I_p<I_n$, whereas if $I_p>I_n$ then CPC<0 and therefore a quantity $CPC_+$ defined by the equation $CPC_+=(I_p/I_n-1)\cdot 100$ describes a stimulation of phagocytosis in percentages.

Figure 6:
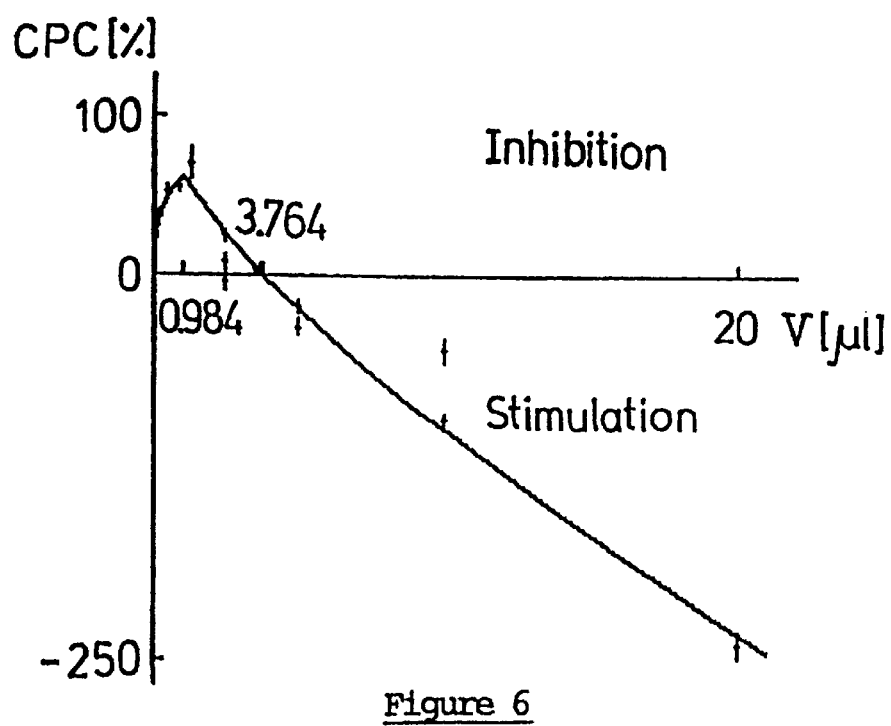
FIG. 6 is a graph showing the volume-dependent modulatory and triggering effect of the peptide-peptone formulation according to the invention on phagocystosis demonstrated by nonmonotonic changes in the CPC (V) function.

With reference to Table 2, in the volume interval [0.167, 0.984] µl interval the changes in the $_pI_n$ or CPC values (as shown in FIG. 6), caused by changes in V (cf. Table 2) are expressed by regressions:

$$I_p/I_n(V)=1-(0.063\pm 0.03)\cdot V^{(0.31\pm 0.06)}, \quad (6)$$

$$CPC(V)=(62.6\pm 2.0)\cdot V^{(0.31\pm 0.06)}, \text{ tm} \quad (7)$$

at a correlation coefficient r=0.96±0.04. Therefore, in the discussed volume interval the inhibition of phagocytosis, caused by the improved Peptide-peptone formulation of the invention, increases with the volume of the formulation used.

According to equations 4 and 7 the inhibition caused by the conventional Peptide-peptone formulation at V=[0.167, 0.984] µl is higher than that by the Peptide-peptone formulation of the invention by 8.8–17.2 percentage points. This means that the redress of the concentration of formulations in the Peptide-peptone formulation of the invention, which absorb in the 200–235 nm interval, is not sufficient for redressing the perturbation of phagocytosis to the level caused by conventional Peptide-peptone formulation. Such 8.8–17.2 percentage point decrease in the perturbation is directly related to the absence of those smaller molecular weight formulations (MW <8–15 kDa) which were removed or dialyzed away according to the invention. Since those smaller molecular weight formulations have an absorption band at 235–300 nm one can conclude that they are peptones and/or their associations with peptides, and state that their contribution to the inhibition of phagocytosis ranges from 8.8 to 17.2%. Consequently the higher molecular weight formulations (MW>8–15 kDa) occurring in the Fraction A peptide formulation according to the invention show an 82.8–91.2 percent contribution to the inhibition phagocytosis in the [0.167, 0.984] µl range.

In a higher range [0.984, 3.764] µl interval the changes in $I_p/I_n$ or CPC (FIG. 6), caused by changes in V (cf. Table 2), are expressed by the regressions:

$$_pI_n(V)=(0.38\pm 0.07)\cdot V^{(0.73\pm 0.11)} \quad (8)$$

$$CPC(V)=[1-(0.38\pm 0.07)\cdot V^{(0.73\pm 0.11)}]100, \quad (9)$$

at a correlation coefficient r=0.94±0.04. There occurs an inhibition of phagocytosis caused by the Fraction A peptide formulation of the invention at V=[0.984,3.764] µl and a stimulation at V>3.764 µl because CPC(3.764)=0.

The Fraction A peptide formulation, according to the invention, inhibits a phagocytosis at V=[0.984, 3.764] µl, although the inhibition decreases to zero, according to Eq. 9, when V increases to 3.764 µl. In comparison with the inhibition caused by conventional Peptide-peptone, there is discerned a difference ranging from 14.4 to 88.0 percentage points. For instance, 3.764 µl of the Peptide-peptone formulation of the invention does not inhibit a phagocytosis (CPC=0) whereas the same volume of conventional Peptide-peptone inhibits phagocytosis to 88.0 percentage points.

Again, peptide peptones appear to be responsible for that inhibition.

The difference between the Fraction A peptide formulation of the invention in comparison to the conventional Peptide-peptone formulation are particularly noticeable at volumes greater than 3.764 µl because the formulation of the invention stimulates a phagocytosis at such volumes, as represented by negative values of CPC in Eq. 8 above, whereas conventional Peptide-peptone continues to inhibit the phagocytosis as reflected by the sample volume of 5.000 µl in Table 1 above showing that the conventional formulation inhibited phagocytosis at 87.2 percentage points.

Whereas negative values of CPC in Eq. 8 above indicate stimulation of phagocytosis, positive values of the CPC (V) function in Eq. 10 below correspondingly indicate stimulation of phagocytosis.

$$CPC_+(V)=[(0.38\pm 0.07)\cdot V^{(0.73\pm 0.11)}-1]\cdot 100. \quad (10)$$

It should be emphasized that the Peptide-peptone formulation according to the invention did not change the phagocytic activity of neutrophils (CPC=0) after the neutrophils have been stimulated by FMLP, i.e., the changes in the phagocytic activity were observed only when neutrophils have been treated by the Peptide-peptone formulation prior to the stimulation by FMLP. For instance, the 245% stimulation of phagocytosis occurring at V=20 µl was possible only when the incubation with the Peptide-peptone formulation preceded the addition of FMLP. This fact indicates the phenomenon of priming. Downey G. P., Fukushima T., Fialkow L. and Waddell T. K., Intracellular Signaling In Neutrophil Priming and Activation, *Sem. In Cell Biol.*, 6, 345–356, 1995. The priming is caused by the active components in the Peptide-peptone formulation with MW>8–15 kDa, because that phenomenon does not occur for the conventional Reticulose™ formulation where it is blocked by the low molecular-weight active components (MW<8–15 kDa), i.e., peptone fragments and their associations with peptides.

Amongst the possible pathways by which the formulations contained in the Peptide-peptone formulation of the invention affect neutrophil phagocytosis, the following are most likely: the influence on a receptor expression; binding of a stimulus (FMLP) with receptors; transduction of a signal to the cell interior; and the activation of NADPH-oxidase. The above-mentioned and other forms of influence on metabolic pathways result in some changes in the production of active forms of oxygen (e.g., $'O_1, O_2^-$) which in turn determine the final stage of phagocytosis.

Conclusions

As understood from the foregoing test results, the conventional Peptide-peptone formulation inhibits a phagocytic activity of neutrophils for all of the investigated volumes. The inhibition decreases linearly ($CPC(V)=2.04 \cdot V+0.32$) in the [0.063, 0.139] $\mu l$ interval, then increases nonlinearly ($CPC(V)=[1-0.23 \cdot V^{-0.49}] \cdot 100$) at V>0.139 $\mu l$ with the conventional formulation used. The inhibitory effect of the conventional formulation on phagocytosis of neutrophils is believed to be caused by peptone fragments (possibly associated with peptides) having a low molecular weight, i.e., MW<8–15 kDa, whereas the Peptide-peptone formulation according to the invention with active components having MW>8–15 kDa stimulate phagocytosis.

Specifically, the Peptide-peptone formulation of the invention inhibits a phagocytic function of isolated human neutrophils at low volumes (<3.674 $\mu l$) of the diluted solution used. The inhibition of phagocytosis increases according to a power law ($CPC(V)-62.6 \cdot V^{0.31}$) for volumes below 0.984 $\mu l$ and then decreases nonlinearly ($CPC(V)=[1-0.38 \cdot V^{0.73}] \cdot 100$) for V>0.984 $\mu l$. At the volume threshold of 3.764 $\mu l$ it causes no inhibition of a phagocytic function of neutrophils, and above such volume threshold it stimulates such phagocytic function. The stimulation changes with the Peptide-peptone formulation volume according to a power low ($CPC_+(V)=[0.38 \cdot V^{0.73}-1] \cdot 100$). Reactive components of the Peptide-peptone formulation according to the invention (peptides without aromatic components) characterized by MW>8–15 kDa and absorption at 200–235 nm, play a role of priming factors, which convert neutrophils to a status more "respondent" to external stimuli such as FMLP.

The presence of peptide peptones with MW<8–15 kDa (as it holds for conventional Peptide-peptone) annihilates the stimulation of phagocytosis by the heavier (MW>8–15 kDa) active components. On the other hand, the Peptide-peptone formulations according to the invention, having mainly stimulatory effects on a phagocytic activity of neutrophils, is obtained by separating away the small peptide peptones (MW<8–15 kDa) by a dialysis or centrifuge of the conventional Peptide-peptone formulation through an appropriate semipermeable membrane, such as a 24 Angstrom membrane or through appropriate centrifugation. Further, the removed or separated lower weight active components (MW<8–15 kDa) can be used in treating auto immune diseases as discussed above. Basically, the lower weight active components of the Peptide-peptone formulation function to slow down the degeneration caused by the auto immune diseases. Moreover, the Peptide-peptone formulation according to the invention can be tailored to treat different viruses by further narrowing a range of molecular weights of the active components contained therein.

Use Of The Peptide-peptone Formulations Of The Invention

The formulations of the present invention are most preferably administered by way of injectable aqueous solutions or preparations, discussed further hereinbelow in relation to specific examples of uses, but may be otherwise administered orally, parenterally, sublingually, by inhalation spray, rectally, or topically in dosage unit formulations containing appropriate non-toxic carriers, adjuvants and vehicles as desired. The term parenteral encompasses subquetaneous injections, intravenous, intramuscular, intraternal injection or infusion techniques.

As an injectable aqueous solution, the Peptide-peptone formulations according to the invention may be packaged in appropriate sized glass ampules similar to manner in which the conventional Peptide-peptone formulation is packaged as discussed above, or in appropriate larger stoppered vials.

According to the invention, different protocols have been developed for treating different viral infections with the Peptide-peptone formulations of the invention. Below are presented four protocols for treating herpes/genital warts; Hepatitis B; Hepatitis C, Chronic Fatigue, Epstein-Barr; and HIV using injectable aqueous solutions of the Peptide-peptone formulations of the invention. According to an important aspect of the invention, as discussed above, the Peptide-peptone formulation may be modified or specifically adapted for treating different viruses.

Protocol No. 1

Have test performed for Herpes A, B and C, include IGG, IGA.

Begin treatment within two days of disease outbreak.

a) Inject Peptide-peptone solution (Immax A) subcutaneously twice daily for seven (7) days—1 mL each injection.

Normal total usage is 30 ml.

Have Herpes test performed for specific Herpes type established in original Herpes panel (have both IGG and IGA performed).

Usage of 1 ml 28 or 29 gauge disposable insulin-type syringes is recommended, and each syringe should be disposed of safely after a single use. The Peptide-peptone solution must be kept out of direct sunlight and may initially be refrigerated, though it need not be. If so, bring the syringe to body temperature before injection (e.g. holding it in hand). Inject slowly to provide painless infusion. If there is pain at injection site because of cold Peptide-peptone or too fast injection, pain will dissipate within 15 minutes. Rotate injection sites. Dosage schedule should be suggested, initiated and monitored by a licensed physician in all cases.

NOTE: 60% Of Herpes patients clear infection using this protocol. The remaining 40% are primarily persons that have a weakened immune system because of stress or other causes such as sunburn. For these patients, it is recommended to provide a maintenance dosage of ½ mL twice a day for one day per month to prevent recurrence.

Protocol No. 2

Life Threatening Diseases-Hepatitis B, Hepatitis C, Chronic Fatigue, Epstein-Barr, Encephalitis, Cancers Have blood tests performed for Hepatitis B or suspected pathogen-include IGG, IGA where appropriate.

Inject Peptide-peptone solution (Immax A)—1 mL subcutaneously two times daily for 7 days.

Inject Peptide-peptone solution—1 mL once daily for the duration of treatment.

Normal total usage is 50 ml.

Do respective blood work 2 months after protocol has been completed to reevaluate condition, and adjust per attending physician's recommendation.

Usage of 1 ml 28 or 29 gauge disposable insulin-type syringes is recommended, and each syringe should be disposed of safely after a single use. The Peptide-peptone solution must be kept out of direct sunlight and may initially be refrigerated, though it need not be. If so, bring the syringe to body temperature before injection (e.g. holding it in hand). Inject slowly to provide painless infusion. If there is pain at injection site because of cold Peptide-peptone or too fast injection, pain will dissipate within 15 minutes. Rotate injection sites. Dosage schedule should be suggested, initiated and monitored by a licensed physician in all cases.

Protocol No. 3—Malaria

Test for presence of pathogen.

Adult—Inject 1 ml Peptone-peptide solution (Immax A) subcutaneously or intra-muscularly once daily for 5 days.

Child less than 12 years—Inject ½ ml Peptide-peptide solution (Immax A) subcutaneously or intra-muscularly once on $1^{st}$ day of treatment. Day 5 repeat.

Usage of 1 ml 28 or 29 gauge disposable insulin-type syringes is recommended, and each syringe should be disposed of safely after a single use. The Peptide-peptone solution must be kept out of direct sunlight and may initially be refrigerated, though it need not be. If so, bring the syringe to body temperature before injection (e.g. holding it in hand). Inject slowly to provide painless infusion. If there is pain at injection site because of cold Peptide-peptone or too fast injection, pain will dissipate within 15 minutes. Rotate injection sites. Dosage schedule should be suggested, initiated and monitored by a licensed physician in all cases.

After treatment a re-evaluation of patient blood counts and clinical signs should be performed by a physician. It is the physician's responsibility to recommend continuation of treatment if indicated.

Protocol No. 4—Dengue Fever

Test blood to confirm presence of suspected pathogen.

Inject 1 ml. Peptide-peptone solution (Immax A) subcutaneously or intramuscularly twice daily for 5 days.

Usage of 1 ml 28 or 29 gauge disposable insulin-type syringes is recommended, and each syringe should be disposed of safely after a single use. The Peptide-peptone solution must be kept out of direct sunlight and may initially be refrigerated, though it need not be. If so, bring the syringe to body temperature before injection (e.g. holding it in hand). Inject slowly to provide painless infusion. If there is pain at injection site because of cold Peptide-peptone or too fast injection, pain will dissipate within 15 minutes. Rotate injection sites. Dosage schedule should be suggested, initiated and monitored by a licensed physician in all cases.

After treatment a re-evaluation of patient blood counts and clinical signs should be performed by a physician. It is the physician's responsibility to recommend continuation of treatment if indicated.

These four exemplary protocols according to the invention reflect the effectiveness of the improved Peptide-peptone formulation in treating many viruses, and auto immune diseases and often are effective in completely eradicating the virus or disease in the patient. Where the virus or disease is not completely eradicated, additional treatment of the virus with the peptide-peptone formulation according to the invention can be determined and tailored to the patient through testing of the patient after administration of the protocol program. With the initial larger dozes provided in the early steps according to the protocols of the invention, patients often promptly realize significant relief from the viruses and diseases.

ADDITIONAL STUDIES OF THE PHYSIOLOGICAL PROPERTIES OF THE COMPOSITIONS ACCORDING TO THE INVENTION

Another study was undertaken comparing the therapeutic effects of a composition according to the heavier weight fraction A composition according to the present invention, sold commercially by Immunotherapy, Inc. under the trademark Immax A, contrasted with results obtained after similar treatment with the conventional peptide-peptone composition, and with results obtained from treatment with a placebo, in treating HIV positive patients.

Effects on CD4 and CD8 T cell counts in blood of an Immax A therapy performed on 9 HIV-positive patients in a first location were statistically analyzed and contrasted with those obtained in HIV-positive placebo patients and in 15 HIV-positive patients treated with the conventional peptide-peptone composition in a second location.

Statistically significant improvements in the CD4 and CD8 T cell counts were observed in the patients treated with the Immax A composition, both 90 and 180 days after treatment was initiated. No statistically significant improvement in T cell counts was observed from treatment with the conventional peptide-peptone composition, while T cell counts decreased in patients treated with a placebo.

Changes in both active and placebo patients at the end of treatment (Day 90 or 120) are as follows: a 54.3% significant ($p<0.09$) increase in CD4 T cell counts and 22.4% significant ($p<0.03$) increase in CD8 T cell counts were found on day 90 of the Immax A therapy in the first location. Neither significant ($p<0.20$) changes in CD4 and CD8 T cell changes were found on day 120 in patients treated with the conventional composition (Immax) in the second location.

Changes in both active and placebo patients after the treatment (Day 180): a 43.7% significant ($p<0.09$) increase in CD4 T cell counts and 8.9% significant ($p<0.17$) increase in CD8 T cell counts were found in the patients treated with Immax A on day 180, i.e. 90 days beyond the completion of treatment. In the placebo patients a 24.7% significant ($p<0.07$) decrease in CD8 T cell counts was found on day 180.

This test clearly shows that surprising physiologically and medically significant benefits were obtained by altering the makeup of the conventional peptide-peptone composition by separating and removing the lower molecular weight components from the higher molecular weight components of the composition.

Further experimental studies have been done showing the efficacy of the improved Fraction A and Fraction B compositions according to the invention in the following areas:

Both of the compositions have been shown to inhibit the peroxidative activity of myeloperoxidase, suggesting possible usefulness as anti-inflammatories. Peptide (Immax A) and peptide-peptone (Immax B) preparations were tested for their ability to modify luminol-enhanced chemiluminescence from the myeloperoxidase-hydrogen peroxide system. Both of the preparations were proven to exert an inhibitory effect on the peroxidative activity of myeloperoxidase. The most probable mechanism underlying these effects are theorized to be scavenging of the myeloperoxidase oxidant intermediates and converting the enzyme to an inactive form. Regardless of the actual mechanism underlying the inhibitory effects of Immax A and Immax B on MPO, the inhibition itself suggests possible application of these preparations in the treatment of inflammatory diseases connected with increased activity of MPO. The anti-inflammatory properties of Immax A and Immax B indicate their possible application:

A) as adjunctive drugs in interferon therapy when the increased release of MPO is observed, B) in MPO-related glomerulonephritis accompanied by the effects of the impaired inactivation of MPO, C) in glomerular capillary necrosis leading to crescentic glomerulonephritis, D) in infections, when neutrophils are excessively stimulated by increased levels of TNF-alpha and IL-6 with consecutive release of MPO;

E) in diseases in which non-steroid anti-inflammatory drugs are necessary to scavenge destructive oxidant products of MPO contributing to inflammation;

F) in diseases with the altered inflammatory response of phagocytic cells to compensate the receptor-mediator reception mechanisms of those cells impaired by MPO;

G) in diseases with a high level of haemolytic C5–9 complex, produced in a chain reaction, the beginning of which (C5) is activated by MPO;

H) in dermatology and cosmetics, to prevent cell injury caused by disruption of liposomes by MPO which occurs at pH<7.0.

Further studies have been done using the compositions according to the invention, and these further studies have shown that:

the Fraction A composition has been confirmed to have a strong antioxidative activity with respect to reactive oxygen species;

both of the compositions have been shown to inhibit the activity of xantine oxidase in vitro, with a tenfold greater affinity of xantine oxidase to the Fraction A composition (Immax A) than to the Fraction B composition (Immax B).

The Cystine Switch

The cystine switch is known to be an important coordinator of human immune response. When the switch is off or neutral, the immune system takes no action, hence a patient is in a chronic state of immune suppression. The immune system is not able to conquer an infection.

Without wishing to be bound by any theory, it is believed that the use of the Fraction A peptide containing composition according to the invention transforms the cystine switch from neutral or negative, to positive. It is believed that moving the cystine switch back to positive, through repeated injections of the inventive composition induces a dormant immune system to function again.

Although there have been described above what are considered to be presently preferred embodiments of the invention, it will be understood as various changes and modifications may be made thereto without departing from the spirit or essence of the invention. The scope of the invention is indicated by the appended claims, rather than by the foregoing description.

I claim:

1. A peptide-containing composition, comprising components having molecular weights in a range from about 8–25 kDa, the composition being a product of a process in which a mixture of casein, blood albumin, beef peptone, nucleic acid, and a base is processed in an aqueous medium at a temperature and pressure elevated above ambient temperature and pressure, and said mixture is separated into fractions based on molecular weight subsequent to said process;

wherein said composition absorbs light in a wavelength interval from about 200–235 nm with a maximum absorbance at 205 nm;

and further wherein said composition is substantially free of components having a molecular weight below 8 kDa.

2. A composition containing peptides and peptones, comprising components having molecular weights in a range from about 0–8 kDa, the composition being a product of a process in which a mixture of casein, blood albumin, beef peptone, nucleic acid, and a base is processed in an aqueous medium at a temperature and pressure elevated above ambient temperature and pressure, and said mixture is separated into fractions based on molecular weight subsequent to said process;

wherein said composition absorbs light in a wavelength infernal from about 235–300 nm, and wherein said composition is substantially free of components having a molecular weight above 8 kDa.

3. A composition according to claim 1, wherein said mixture contains 40–50 weight % casein; 1–10 weight % blood albumin, 15–40 weight % beef peptone, 10–25 weight % nucleic acid and 5–25% base.

4. A method of preparing a peptide containing composition, comprising the steps of:

combining selected ingredients comprising casein, blood albumin, beef peptone, nucleic acid and a base in an aqueous medium to form a process solution;

processing the combined ingredients at an elevated temperature and an elevated pressure with respect to ambient temperature and pressure; and further processing the process solution to separate components having a molecular weight of less than 8 kDa from components having a molecular weight above 8 kDa.

5. A method according to claim 4, wherein said step of further processing is performed in multiple stages, including an initial separating stage which results in a composition having components of varying molecular weights ranging from approximately 1–25 kDa, and a secondary separating stage resulting in a composition containing components having molecular weights exclusively in a range of approximately 8–25 kDa.

6. A method according to claim 5, wherein said aqueous medium in which the components are combined comprises distilled water.

7. A method according to claim 5, wherein said secondary separating stage comprises dialyzing the composition through a membrane having an average pore size of 10–40 Angstroms.

8. A method according to claim 5, wherein said further processing step includes a third separating stage resulting in a composition containing components having molecular weights exclusively in a range of approximately 15–25 kDa.

9. A method according to claim 4, wherein said combining step involves combining the ingredients in the following weight percentages:

casein 30–60%;
blood albumin 1–5%;
beef peptone 10–40%;
nucleic acid 5–25%; and
base 5–25%.

10. A method according to claim 6, wherein said step of processing the combined ingredients involves use of a steam autoclave at a pressure of 5–15 pounds.

* * * * *